United States Patent
Liu et al.

(10) Patent No.: US 11,124,613 B2
(45) Date of Patent: Sep. 21, 2021

(54) RESIN COMPOSITION AND USES OF THE SAME

(71) Applicant: TAIWAN UNION TECHNOLOGY CORPORATION, Chupei (TW)

(72) Inventors: Shur-Fen Liu, Chupei (TW); Chin-Hsien Hung, Chupei (TW)

(73) Assignee: TAIWAN UNION TECHNOLOGY CORPORATION, Chupei (TW)

( * ) Notice: Subject to any disclaimer, the term of this patent is extended or adjusted under 35 U.S.C. 154(b) by 148 days.

(21) Appl. No.: 16/575,810

(22) Filed: Sep. 19, 2019

(65) Prior Publication Data
US 2020/0377676 A1    Dec. 3, 2020

(30) Foreign Application Priority Data
May 31, 2019   (TW) .................................. 108118988

(51) Int. Cl.
| | | |
|---|---|---|
| C08J 3/24 | (2006.01) | |
| C08G 65/48 | (2006.01) | |
| C08L 71/12 | (2006.01) | |
| C08K 5/03 | (2006.01) | |
| C08K 3/36 | (2006.01) | |
| C07D 251/32 | (2006.01) | |
| B32B 15/08 | (2006.01) | |
| C08J 5/24 | (2006.01) | |
| C08K 5/3492 | (2006.01) | |
| C08K 5/14 | (2006.01) | |

(52) U.S. Cl.
CPC ................. *C08J 3/24* (2013.01); *B32B 15/08* (2013.01); *C07D 251/32* (2013.01); *C08G 65/485* (2013.01); *C08J 5/24* (2013.01); *C08K 3/36* (2013.01); *C08K 5/03* (2013.01); *C08K 5/14* (2013.01); *C08K 5/34924* (2013.01); *C08L 71/126* (2013.01); *C08J 2371/12* (2013.01); *C08J 2409/06* (2013.01); *C08L 2201/02* (2013.01)

(58) Field of Classification Search
CPC ..... C08L 71/12; C08L 71/126; C09D 171/12; C09J 171/12; C08G 65/44; C08G 65/485; C08K 5/34924; C08K 5/0025; C08J 3/24
See application file for complete search history.

(56) References Cited

U.S. PATENT DOCUMENTS

| | | | | |
|---|---|---|---|---|
| 5,087,655 A | * | 2/1992 | Okamoto .................. | C08K 7/08 524/432 |
| 9,243,164 B1 | * | 1/2016 | Almen ...................... | C08K 5/03 |
| 9,809,690 B2 | | 11/2017 | Koes | |
| 10,023,707 B2 | | 7/2018 | Liao et al. | |
| 2016/0297988 A1 | | 10/2016 | Liu et al. | |
| 2017/0009061 A1 | * | 1/2017 | Cai ......................... | H01B 3/441 |

FOREIGN PATENT DOCUMENTS

| | | | |
|---|---|---|---|
| CN | 109762115 A | 5/2019 | |
| JP | 2003-002992 A | 1/2003 | |
| JP | 2005-238477 A | 9/2005 | |
| JP | 2017-002296 A | 1/2017 | |
| TW | 201638182 A | 11/2016 | |
| WO | WO-2020196718 A1 * | 10/2020 | ............... H05K 1/03 |

OTHER PUBLICATIONS

Partial machine translation of WO-2020196718-A1 (2020).*
Taiwanese Office Action from Taiwanese Patent Application No. 108118988, dated Dec. 27, 2019.
Taiwan Office Action received in Taiwan Application No. 108118988 dated Oct. 21, 2020.

* cited by examiner

*Primary Examiner* — Kregg T Brooks
(74) *Attorney, Agent, or Firm* — Greer, Burns & Crain, Ltd

(57) ABSTRACT

A resin composition and uses of the same are provided. The resin composition includes the following components:

(A) a cross-linking agent of the following formula (I):

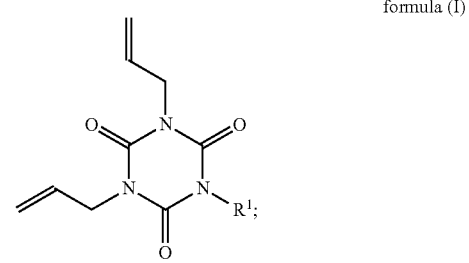

formula (I)

(B) a polyphenylene ether resin, wherein the terminal ends of the polyphenylene ether resin are independently modified by a substituent with a carbon-carbon double bond; and (C) a catalyst, wherein, $R^1$ in formula (I) is a $C_6$ to $C_{16}$ alkyl or a $C_6$ to $C_{16}$ alkenyl, and the weight ratio of the polyphenylene ether resin (B) to the cross-linking agent (A) ranges from 0.5 to 5.

19 Claims, No Drawings

RESIN COMPOSITION AND USES OF THE SAME

CLAIM FOR PRIORITY

This application claims the benefit of Taiwan Patent Application No. 108118988 filed on May 31, 2019, the subject matters of which are incorporated herein in their entirety by reference.

BACKGROUND

Field of the Invention

The present invention provides a resin composition, especially a polyphenylene ether-based resin composition that comprises a cross-linking agent with a specific structure.

The present invention also provides a prepreg and a laminate provided by using the resin composition.

Descriptions of the Related Art

Printed circuit boards (PCBs) are substrates of electronic devices for carrying multiple electronic members that are electrically connected with each other to provide a stable circuit working environment. A printed circuit board is manufactured from a laminate which is formed of alternatively laminated conductive layers and dielectric layers. A printed circuit board can be prepared by the following method.

First, a reinforcing material (e.g., a glass-fiber fabrics) is impregnated into a resin (e.g., an epoxy resin). The resin-impregnated reinforcing material is then cured to a semi-cured state (known as B-stage) to obtain a prepreg. Afterwards, a predetermined number of prepregs are superimposed to provide a dielectric layer. A conductive layer (e.g., a metal foil) is superimposed on at least one external surface of the dielectric layer to provide a superimposed object. Then, the superimposed object is subjected to a hot-pressing operation (known as C-stage) to obtain a laminate. The conductive layer at the surface of the laminate is etched to form a predetermined circuit pattern. Finally, the etched laminate is subjected to a drilling process to form a plurality of holes thereon, and a conductive material is plated on such holes to form via holes, thereby, obtaining the printed circuit board.

In light of trends in the miniaturization of electronic devices, printed circuit boards need to be thinner and denser, as well as meet high-frequency and high-speed transmission requirements. At present, electronic materials prepared by using a fluororesin composition or a polyphenylene ether resin composition are used because electronic materials prepared by using an epoxy resin composition cannot meet the requirements.

A polyphenylene ether resin composition usually contains an isocyanurate compound with a carbon-carbon double bond or a cyanurate compound with a carbon-carbon double bond as a cross-linking agent. Such a cross-linking agent can be found in JP 2003-002992 A and JP 2005-238477 A and is useful in the curing of elastomers or thermoplastic resins. Examples of the isocyanurate compound with a carbon-carbon double bond or cyanurate compound with a carbon-carbon double bond include triallyl isocyanurate (TAIC) and triallyl cyanurate (TAC). For example, U.S. Pat. No. 10,023,707 B2 discloses a thermal-curable polyphenylene ether resin composition comprising TAIC or TAC as a cross-linking agent, wherein TAIC is preferred in terms of thermal resistance and chemical resistance.

However, TAIC and TAC are usually in the form of a liquid monomer with high fluidity, which is unfavorable for mass production or continuous production because runback is observed when impregnating a reinforcing material with a resin composition containing TAIC and TAC. In addition, during the preparation of prepregs, TAIC monomers can evaporate and thus, cause environmental pollution or make the physicochemical properties of the laminates prepared from the prepregs inconsistent with each other. To solve the aforementioned problems, U.S. Pat. No. 9,809,690 B2 discloses a circuit material, wherein TAIC monomers or TAC monomers are polymerized into particles and then added into a resin composition as a filler, thereby, solving the evaporation problem. Nevertheless, the fluidity of the prepreg thus prepared during a hot-pressing operation will inevitably deteriorate.

In view of the above, there is still a need for a resin composition that is easy-to-process, stable and capable of providing an electronic material with outstanding peel strength and dielectric properties.

SUMMARY

The present invention provides a thermal-curable resin composition as well as a prepreg and laminate prepared by using the thermal-curable resin composition. The present invention will address the problems with conventional resin compositions containing TAIC or TAC as a cross-linking agent; that is, it will address the shortcoming of where the electronic material does not have consistent physicochemical properties and are difficult to process. The technical means of the present invention is to use a specific diallyl isocyanurate compound in a polyphenylene ether resin composition as a cross-linking agent. The resin composition of the present invention is easy-to-process and stable, and the electronic material prepared from the resin composition of the present invention is provided with outstanding peel strength and dielectric properties. Thus, the present invention involves the following inventive objectives.

An objective of the present invention is to provide a resin composition, which comprises the following components:

(A) a cross-linking agent of the following formula (I):

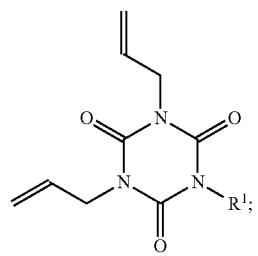

formula (I)

(B) a polyphenylene ether resin, wherein the terminal ends of the polyphenylene ether resin are independently modified by a substituent with a carbon-carbon double bond; and
(C) a catalyst,
wherein,
in formula (I), $R^1$ is a $C_6$ to $C_{16}$ alkyl or a $C_6$ to $C_{16}$ alkenyl, preferably a $C_6$ to $C_{14}$ alkyl or a $C_6$ to $C_{14}$ alkenyl, and more preferably a $C_8$ to $C_{14}$ alkyl or a $C_8$ to $C_{14}$ alkenyl; and the weight ratio of the polyphenylene ether resin (B) to the cross-linking agent (A) ranges from 0.5 to 5, and preferably from 0.8 to 4.

In some embodiments of the present invention, the cross-linking agent (A) is selected from the group consisting of

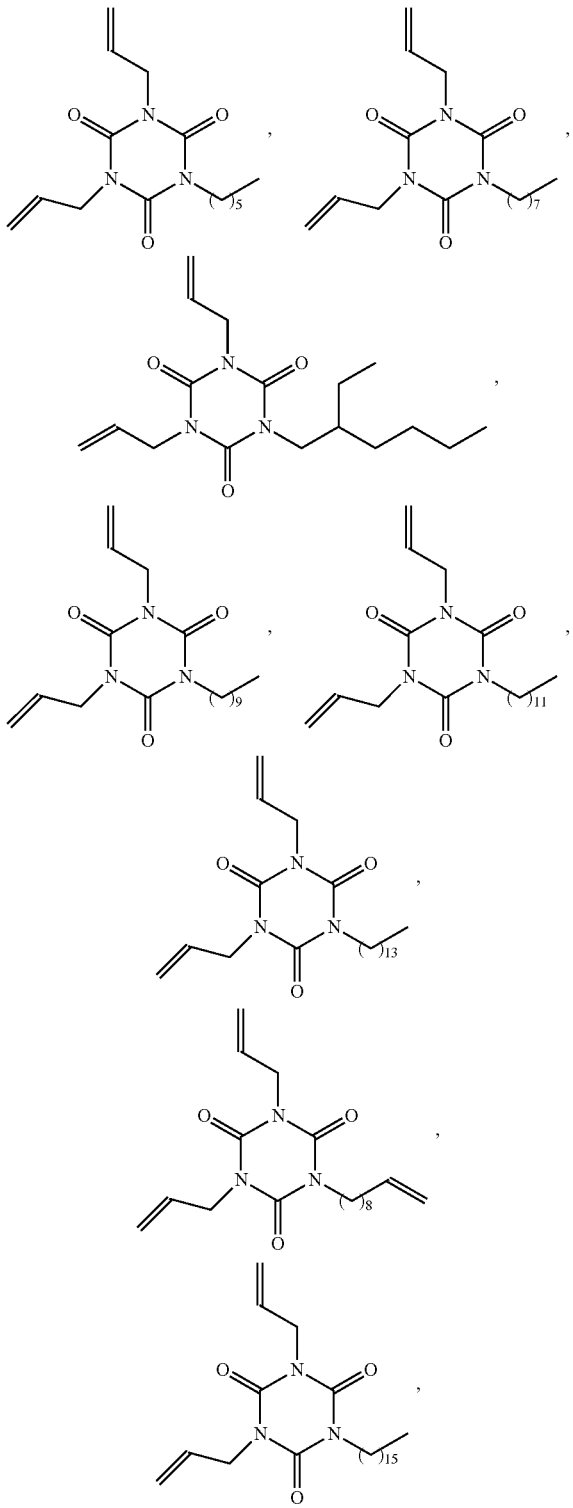

and combinations thereof.

In some embodiments of the present invention, the substituent with a carbon-carbon double bond is represented by the following formula (III):

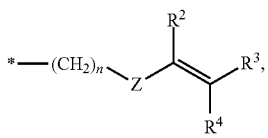

in formula (III),
$R^2$, $R^3$ and $R^4$ are independently H or a substituted or unsubstituted $C_1$ to $C_6$ alkyl;
Z is

or an arylene;
n is an integer ranging from 0 to 10; and
* denotes the bonding site to the terminal end of the polyphenylene ether resin.

In some embodiments of the resent invention the substituent with a carbon-carbon double bond is

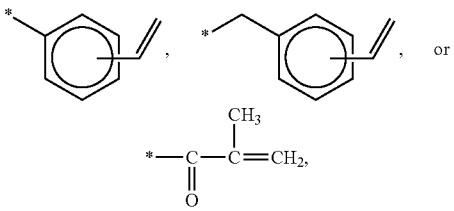

wherein * denotes the bonding site to the terminal end of the polyphenylene ether resin.

In some embodiments of the present invention, the catalyst (C) is an organic peroxide. The organic peroxide may be selected from the group consisting of dicumyl peroxide (DCP), tert-butyl peroxybenzoate, di-tert-amyl peroxide (DTAP), isopropylcumyl-tert-butyl peroxide, tert-butylcumylperoxide, di(isopropylcumyl) peroxide, di-tert-butyl peroxide, α,α'-bis(tert-butylperoxy)diisopropyl benzene, benzoyl peroxide (BPO), 1,1-bis(tert-butylperoxy)-3,3,5-trimethylcyclohexane, butyl 4,4-di(tert-butylperoxy) valerate, 2,5-dimethyl-2,5-di(tert-butylperoxy) hexane, 2,5-dimethyl-2,5-di(tert-butylperoxy)-3-hexyne, and combinations thereof.

In some embodiments of the present invention, the resin composition further comprises one or more additives selected from the group consisting of an elastomer, a flame retardant, a filler, a hardening promoter, a dispersing agent, a toughener, a viscosity modifier, a thixotropic agent, a defoaming agent, a leveling agent, a surface treating agent, a stabilizer, and an antioxidant. The elastomer may be selected from the group consisting of polybutadiene, polyisoprene, a styryl-containing polymer, and combinations thereof. The elastomer is preferably a butadiene-styrene copolymer or an isoprene-styrene copolymer. The flame retardant may be a phosphorus-containing flame retardant, a bromine-containing flame retardant, or a combination thereof. The filler may be selected from the group consisting of silica (including hollow silica), aluminum oxide, magnesium oxide, magnesium hydroxide, calcium carbonate, talc, clays, aluminum nitride, boron nitride, aluminum hydroxide, silicon aluminum carbide, silicon carbide, sodium carbonate, titanium dioxide, zinc oxide, zirconium oxide, quartzes, diamonds, diamond-like carbon, graphites, calcined kaolin, pryan, micas, hydrotalcite, polytetrafluoroethylene (PTFE) powders, glass beads, ceramic whiskers, carbon nanotubes, nanosized inorganic powders, and combinations thereof.

Another objective of the present invention is to provide a prepreg, which is prepared by impregnating a substrate with the aforementioned resin composition or by coating the aforementioned resin composition onto a substrate and drying the impregnated or coated substrate.

In some embodiments of the present invention, the substrate is selected from the group consisting of a glass fiber cloth, a kraft paper, a short fiber cotton paper, a natural fiber cloth, an organic fiber cloth, and a composite of two or more of the foregoing.

Yet another objective of the present invention is to provide a laminate, which comprises a dielectric layer and a conductive layer covering the surface of the dielectric layer, wherein the dielectric layer is provided by the aforementioned prepreg. In some embodiments of the present invention, the conductive layer is a copper foil.

To render the above objectives, the technical features and advantages of the present invention more apparent, the present invention will be described in detail with reference to some embodiments hereinafter.

BRIEF DESCRIPTION OF THE DRAWINGS

Not applicable.

DETAILED DESCRIPTION

Hereinafter, some embodiments of the present invention will be described in detail. However, without departing from the spirit of the present invention, the present invention may be embodied in various embodiments and should not be limited to the embodiments described in the specification.

Unless it is additionally explained, the expressions "a," "the," or the like recited in the specification (especially in the claims) should include both the singular and the plural forms.

Unless it is additionally explained, while describing the components in the solution, mixture and composition in the specification, the amount of each component is calculated based on the solid content, i.e., regardless of the weight of the solvent.

The present invention provides a resin composition using polyphenylene ether resin, a cross-linking agent with a modified diallyl isocyanurate structure, and a catalyst to provide an electronic material with satisfactory physicochemical properties and dielectric properties as well as outstanding peel strength. In addition, since the volatility of the cross-linking agent with the modified diallyl isocyanurate structure is low, the resin composition of the present invention is easy-to-process and stable; thus, it is favorable for mass production in industry.

The components and preparation method of the resin composition of the present invention are described in detail in the following.

1. Resin Composition

The resin composition of the present invention comprises a cross-linking agent (A), a polyphenylene ether resin (B) and a catalyst (C) as necessary components, and other optional components.

1.1. Cross-Linking Agent (A)

As used herein, a cross-linking agent denotes a component that has unsaturated functional groups and can react with other components having unsaturated functional groups (e.g., polyphenylene ether resin with modified terminal ends) to carry out a cross-linking reaction to form a steric network structure. In general, cross-linking agents may be classified into monofunctional cross-linking agents and polyfunctional cross-linking agents according to the number of the unsaturated groups contained therein, wherein a monofunctional cross-linking agent has only one unsaturated functional group, while a polyfunctional cross-linking agent has at least two unsaturated functional groups. A polyfunctional cross-linking agent is preferred to make the cured product of a resin composition with a higher cross-linking density. In the resin composition of the present invention, the cross-linking agent (A) is a polyfunctional cross-linking agent with a specific structure. Specifically, the cross-linking agent (A) is represented by the following formula (I):

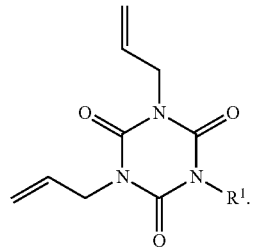

formula (I)

In formula (I), $R^1$ is a $C_6$ to $C_{16}$ alkyl or a $C_6$ to $C_{16}$ alkenyl. Examples of $C_6$ to $C_{16}$ alkyl include but are not limited to n-hexyl, isohexyl, n-heptyl, isoheptyl, n-octyl, isooctyl, n-nonyl, isononyl, n-decyl, isodecyl, n-undecyl, isoundecyl, n-dodecyl, isododecyl, n-tridecyl, isotridecyl, n-tetradecyl, isotetradecyl, n-pentadecyl, isopentadecyl, n-hexadecyl, and isohexadecyl. Examples of $C_6$ to $C_{16}$ alkenyl include but are not limited to 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradeceny, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, 14-pentadecenyl, 1-hexadecenyl, 2-hexadecenyl, 3-hexadecenyl, 4-hexadecenyl, 5-hexadecenyl, 6-hexadecenyl, 7-hexadecenyl, 8-hexadecenyl, 9-hexadecenyl, 10-hexadecenyl, 11-hexadecenyl, 12-hexadecenyl, 13-hexadecenyl, 14-hexadecenyl, and 15-hexadecenyl. In the preferred embodiments of the present invention, $R^1$ is a $C_8$ to $C_{14}$ alkyl or a $C_8$ to $C_{14}$ alkenyl. Examples of $C_8$ to $C_{14}$ alkyl include the aforementioned examples of $C_6$ to $C_{16}$ alkyls with carbon number ranging from 8 to 14, and examples of $C_8$ to $C_{14}$ alkenyl include the aforementioned examples of $C_6$ to $C_{16}$ alkenyls with carbon number ranging from 8 to 14.

Specific examples of the cross-linking agent (A) with a structure of formula (I) include but are not limited to 1,3-diallyl-5-hexyl isocyanurate, 1,3-diallyl-5-heptyl isocyanurate, 1,3-diallyl-5-octyl isocyanurate, 1,3-diallyl-5-isooctyl isocyanurate, 1,3-diallyl-5-nonyl isocyanurate, 1,3-diallyl-5-decyl isocyanurate, 1,3-diallyl-5-undecyl isocyanurate, 1,3-diallyl-5-dodecyl isocyanurate, 1,3-diallyl-5-tetradecyl isocyanurate, 1,3-diallyl-5-hexadecyl isocyanurate, 1,3-diallyl-5-hexenyl isocyanurate, 1,3-diallyl-5-heptenyl isocyanurate, 1,3-diallyl-5-octenyl isocyanurate, 1,3-diallyl-5-decenyl isocyanurate, 1,3-diallyl-5-dodecenyl isocyanurate, and 1,3-diallyl-5-tetradecenyl isocyanurate.

In some embodiments of the present invention, the cross-linking agent (A) is selected from the group consisting of

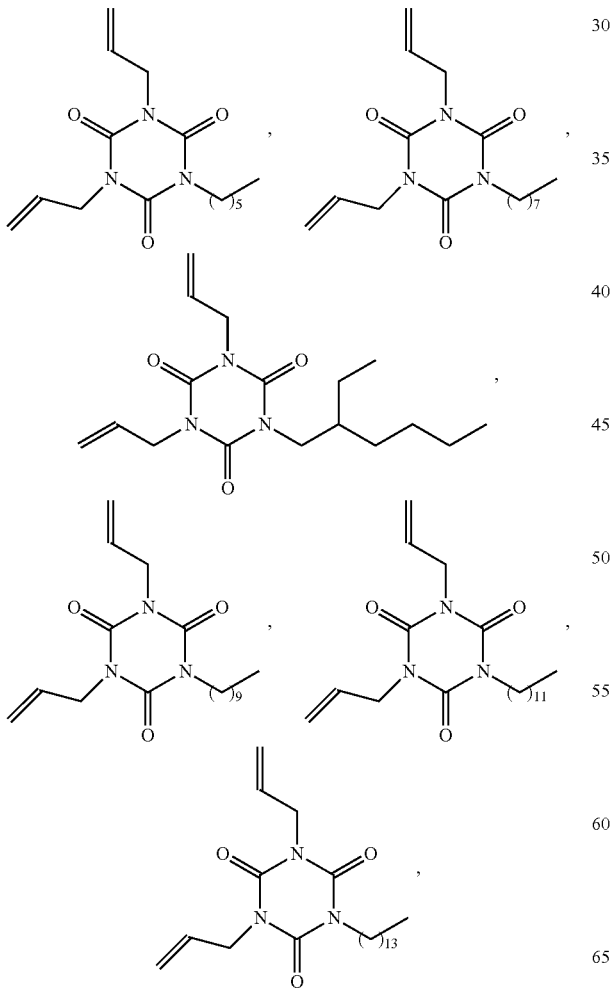

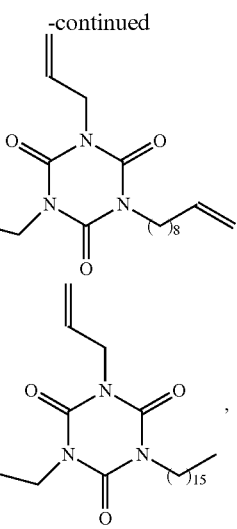

and combinations thereof. In the appended examples,

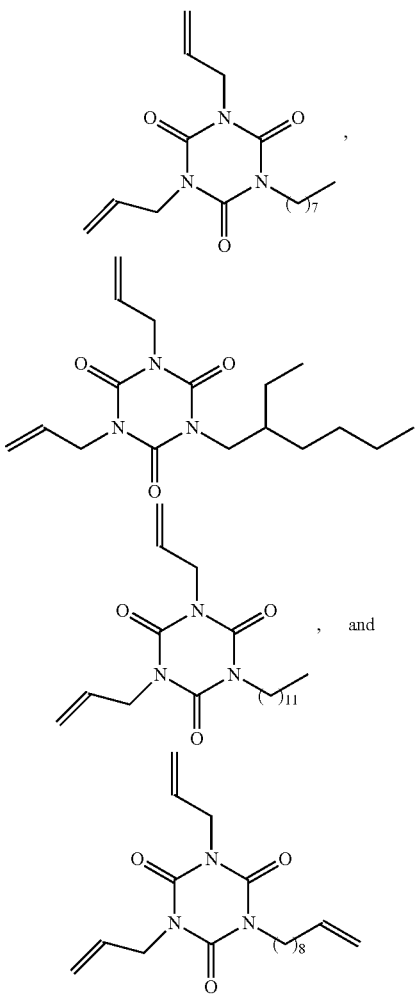

are used.

The cross-linking agent (A) of formula (I) can be obtained by reacting diallyl isocyanurate with a hydrocarbyl halide in the presence of a catalyst. Examples of the hydrocarbyl halide include but are not limited to hydrocarbyl bromides, such as 1-bromohexane, 1-bromoheptane, 1-bromooctane, 1-bromononane, 1-bromodecane, 1-bromoundecane, 1-bromododecane, 1-bromotetradecane, 1-bromohexadecane, 1-bromo-isobutane, 1-bromo-isopentane, 1-bromo-isohexane, 1-bromo-isoheptane, 1-bromo-isooctane, 1-bromo-isononane, 1-bromo-isodecane, 1-bromo-isoundecane, 1-bromo-isododecane, 1-bromo-isotetradecane, 1-bromo-isohexadecane, 4-bromo-1-butene, 5-bromo-1-pentene, 6-bromo-1-hexene, 7-bromo-1-heptene, 8-bromo-1-octene, 9-bromo-1-nonene, 10-bromo-1-decene, 11-bromo-1-undecene, 12-bromo-1-dodecene, 14-bromo-1-tetradecene, and 16-bromo-1-hexadecene. Examples of the catalyst include but are not limited to potassium carbonate, potassium hydroxide, sodium carbonate, and sodium hydroxide. Detailed preparation of the cross-linking agent (A) of formula (I) will be illustrated in the appended examples.

In the resin composition of the present invention, based on the total solid content of the resin composition, the content of the cross-linking agent (A) can range from 5 wt % to 65 wt %, preferably from 8 wt % to 60 wt %, more specifically from 10 wt % to 55 wt %, such as 12 wt %, 15 wt %, 17 wt %, 20 wt %, 22 wt %, 25 wt %, 28 wt %, 30 wt %, 32 wt %, 35 wt %, 37 wt %, 40 wt %, 43 wt %, 45 wt %, 48 wt %, 50 wt %, or 53 wt %. If the content of the cross-linking agent (A) is above the aforementioned range (e.g., higher than 60 wt %), the electronic material prepared from the resin composition may not have good dielectric properties, for example, the electronic material may have an overly high dissipation factor (Df) value. On the other hand, if the content of the cross-linking agent (A) is below the aforementioned range (e.g., lower than 10 wt %), the cross-linking density of the cured product of the resin composition may not be effectively enhanced, thereby adversely affecting the thermal resistance of the electronic material prepared therefrom.

1.2. Polyphenylene Ether Resin (B)

The polyphenylene ether resin (B) is one of the essential components of the resin composition of the present invention, wherein the terminal ends of the polyphenylene ether resin are independently modified by a substituent with a carbon-carbon double bond. Specifically, the polyphenylene ether resin (B) is a thermal-curable resin that has at least a repeating unit of the following formula (II) in the molecular main chain:

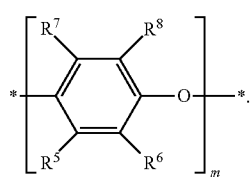

formula (II)

In formula (II), $R^5$, $R^6$, $R^7$ and $R^8$ are independently H, alkyl, alkenyl, alkynyl, formyl, alkylcarbonyl, alkenylcarbonyl, or alkynylcarbonyl; m is an integer ranging from 1 to 50; and * denotes the bonding site to a substituent with a carbon-carbon double bond. It is preferred that $R^5$, $R^6$, $R^7$ and $R^8$ are independently H, $C_1$ to $C_{18}$ alkyl, $C_2$ to $C_{18}$ alkenyl, $C_2$ to $C_{18}$ alkynyl, $C_2$ to $C_{18}$ alkylcarbonyl, $C_3$ to $C_{18}$ alkenylcarbonyl, or $C_3$ to $C_{18}$ alkynylcarbonyl. Examples of $C_1$ to $C_{18}$ alkyl include but are not limited to methyl, ethyl, n-propyl, isopropyl, n-butyl, isobutyl, tert-butyl, n-pentyl, isopentyl, tert-pentyl, neopentyl, and the above-mentioned examples of $C_6$ to $C_{16}$ alkyl. Examples of $C_2$ to $C_{18}$ alkenyl include but are not limited to vinyl, propenyl, allyl, 1-butenyl, 2-butenyl, 3-butenyl, isobutenyl, 1-pentenyl, 2-pentenyl, 3-pentenyl, 4-pentenyl, and the above-mentioned examples of $C_6$ to $C_{16}$ alkenyl. Examples of $C_2$ to $C_{18}$ alkynyl include but are not limited to ethynyl, propynyl, propargyl, 1-n-butynyl, 2-butynyl, isobutynyl, 1-pentynyl, 1-hexynyl, 1-heptynyl, 1-octynyl, 1-nonynyl, 1-decynyl, 1-undecynyl, 1-dodecynyl, 1-tridecynyl, 1-tetradecynyl, 1-pentadecynyl, and 1-hexadecynyl. Examples of $C_2$ to $C_{18}$ alkylcarbonyl include but are not limited to acetyl, propionyl, isobutyryl, and cyclohexylformyl. Examples of $C_3$ to $C_{18}$ alkenylcarbonyl include but are not limited to acryloyl and methylacryloyl. Examples of $C_3$ to $C_{18}$ alkynylcarbonyl include but are not limited to propioloyl.

The terminal ends of the polyphenylene ether resin (B) are independently modified by a substituent with a carbon-carbon double bond. Specifically, the substituent with a carbon-carbon double bond that is used for modifying the polyphenylene ether resin (B) is represented by the following formula (III):

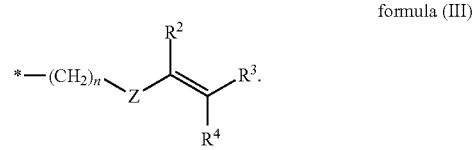

formula (III)

In formula (III), $R^2$, $R^3$ and $R^4$ are independently H or a substituted or unsubstituted $C_1$ to $C_6$ alkyl; Z is

or a substituted or unsubstituted arylene; n is an integer ranging from 0 to 10; and * denotes the bonding site to the terminal end of the polyphenylene ether resin. It is preferred that $R^2$, $R^3$ and $R^4$ are independently H or substituted or unsubstituted methyl; and n is an integer ranging from 0 to 6. Examples of arylene include but are not limited to phenylene and naphthylene.

In formula (III), when n is 0, it denotes that Z is directly bonded to the terminal ends of the polyphenylene ether. In some embodiments of the present invention, the substituent with a carbon-carbon double bond is

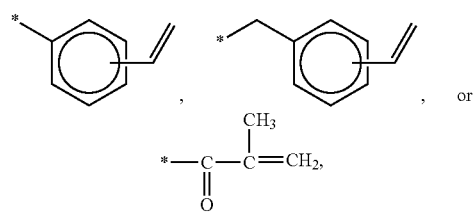

wherein * denotes the bonding site to the terminal end of the polyphenylene ether resin. In the appended examples, the terminal ends of the polyphenylene ether resin (B) are modified by

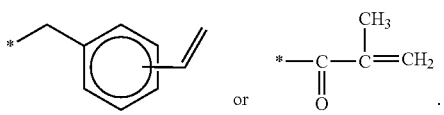

In the resin composition of the present invention, the number average molecular weight (Mn) of the polyphenylene ether resin (B) may range from 1000 to 7000, preferably from 1000 to 5000, more specifically from 1000 to 3000, such as 1200, 1300, 1400, 1500, 1600, 1700, 1800, 1900, 2000, 2100, 2200, 2300, 2400, 2500, 2600, 2700, 2800, or 2900. If the Mn of the polyphenylene ether resin (B) is above the aforementioned range, the resin composition may have unsatisfactory formability (fluidity), solubility, and the like, thereby causing problems during processing. By contrast, if the Mn of the polyphenylene ether resin (B) is below the aforementioned range, the resin composition may have unsatisfactory thermal resistance and dielectric properties.

In the resin composition of the present invention, based on the total solid content of the resin composition, the content of the polyphenylene ether resin (B) may range from 15 wt % to 88 wt %, preferably from 20 wt % to 85 wt %, more specifically from 25 wt % to 80 wt %, such as 26 wt %, 28 wt %, 30 wt %, 32 wt %, 34 wt %, 35 wt %, 36 wt %, 38 wt %, 40 wt %, 42 wt %, 45 wt %, 46 wt %, 48 wt %, 50 wt %, 52 wt %, 55 wt %, 58 wt %, 60 wt %, 62 wt %, 65 wt %, 68 wt %, 70 wt %, 72 wt %, 75 wt %, or 78 wt %.

In the resin composition of the present invention, the weight ratio of the polyphenylene ether resin (B) to the cross-linking agent (A) preferably ranges from 0.5 to 5, more specifically from 0.8 to 4, such as 0.82, 0.85, 0.88, 0.9, 0.92, 0.95, 0.98, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, or 3.9. When the weight ratio of the polyphenylene ether resin (B) to the cross-linking agent (A) is within the aforementioned range, the cross-linking of the resin composition is perfect in providing outstanding adhesive strength and thereby the electronic material prepared from the resin composition can be provided with outstanding peel strength (including normal temperature peel strength and heat resistant peel strength) without sacrificing other properties.

1.3. Catalyst (C)

As used herein, a catalyst denotes a component that can promote the cross-linking reaction of the resin composition and lower the curing reaction temperature of the resin composition. The type of the catalyst is not particularly limited as long as it can promote the cross-linking reaction and lower the curing reaction temperature. Suitable examples of the catalyst include but are not limited to organic peroxides, such as a compound with a structure of $R^9$—O—O—$R^{10}$ or $R^9$—O—O—$R^{11}$—O—O—$R^{10}$. $R^9$ and $R^{10}$ are independently a hydrocabyl or benzoyl, preferably independently a $C_1$ to $C_{20}$ alkyl, a $C_6$ to $C_{20}$ aryl, a $C_7$ to $C_{20}$ aralkyl, or a $C_7$ to $C_{20}$ alkylaryl, and more preferably independently a $C_1$ to $C_{12}$ alkyl, a $C_6$ to $C_{12}$ aryl, a $C_7$ to $C_{12}$ aralkyl, or a $C_7$ to $C_{12}$ alkylaryl. $R^{11}$ is a hydrocarbylene, preferably a $C_1$ to $C_{20}$ alkylene, a $C_6$ to $C_{20}$ arylene, a $C_7$ to $C_{20}$ arylenealkyl, or a $C_7$ to $C_{20}$ alkylenearyl, and more preferably a $C_1$ to $C_{12}$ alkylene, a $C_6$ to $C_{12}$ arylene, a $C_7$ to $C_{12}$ arylenealkyl, or a $C_7$ to $C_{12}$ alkylenearyl. The arylenealkyl or arylenealkyl denotes a divalent aralkyl or alkylaryl in which one bonding site is located on its aryl moiety and the other bonding site is located on its alkyl moiety.

Examples of the organic peroxide include but are not limited to dicumyl peroxide, tert-butyl peroxybenzoate, di-tert-amyl peroxide, isopropylcumyl-tert-butyl peroxide, tert-butylcumylperoxide, di(isopropylcumyl) peroxide, di-tert-butyl peroxide, α,α'-bis(tert-butylperoxy)diisopropyl benzene, benzoyl peroxide, 1,1-bis(tert-butylperoxy)-3,3,5-trimethylcyclohexane, butyl 4,4-di(tert-butylperoxy)valerate, 2,5-dimethyl-2,5-di(tert-butylperoxy) hexane, and 2,5-dimethyl-2,5-di(tert-butylperoxy)-3-hexyne. The above-mentioned organic peroxides can either be used alone or in any combination. In the appended examples, α,α'-bis(tert-butylperoxy)diisopropyl benzene is used as the catalyst (C).

In the resin composition of the present invention, based on the total solid content of the resin composition, the content of the catalyst (C) may range from 0.05 wt % to 3 wt %, more specifically from 0.1 wt % to 2 wt %, such as 0.3 wt %, 0.5 wt %, 0.7 wt %, 0.8 wt %, 1 wt %, 1.2 wt %, 1.5 wt %, or 1.8 wt %.

1.4. Optional Components

The resin composition of the present invention may further comprise optional components, such as an elastomer, a flame retardant, a filler, a hardening promoter which will be illustrated below, and additives known in the art, to adaptively improve the workability of the resin composition during processing or improve the physicochemical properties and flame retardance of the electronic material prepared from the resin composition. Examples of the additives known in the art include but are not limited to a dispersing agent, a toughener, a viscosity modifier, a thixotropic agent, a defoaming agent, a leveling agent, a surface treating agent, a stabilizer, and an antioxidant.

[Elastomer]

As used herein, an elastomer denotes a polymer with viscoelasticity that can impart toughness to electronic materials. The resin composition of the present invention may further comprise an elastomer to provide an electronic material with better toughness as well as a lower dielectric constant (Dk) and Df. The elastomer preferably has unsaturated functional groups so that it can perform a cross-linking reaction with other components that have unsaturated functional groups. Examples of the elastomer include but are not limited to polybutadiene, polyisoprene, and a styryl-containing polymer. Each of the mentioned elastomers can be used either alone or in any combination. Examples of the styryl-containing polymer include but are not limited to a butadiene-styrene copolymer or an isoprene-styrene copolymer. In the appended examples, a butadiene-styrene copolymer is used as the elastomer.

In the resin composition of the present invention, based on the total solid content of the resin composition, the content of the elastomer may range from 0 wt % to 30 wt %, preferably from 1 wt % to 20 wt %, more specifically from 1.5 wt % to 15 wt %, such as 1.8 wt %, 2 wt %, 2.3 wt %, 2.5 wt %, 2.8 wt %, 3 wt %, 3.5 wt %, 4 wt %, 5 wt %, 6 wt %, 7 wt %, 8 wt %, 9 wt %, 10 wt %, 11 wt %, 12 wt %, 13 wt %, or 14 wt %.

[Flame Retardant]

In general, adding a flame retardant in the resin composition can enhance the flame retardance of the electronic material prepared from the resin composition. Examples of the flame retardant include but are not limited to a phosphorus-containing flame retardant and a bromine-containing flame retardant. The phosphorus-containing flame retardant and the bromine-containing flame retardant can be used either alone or together with each other. Examples of the phosphorus-containing flame retardant include but are not limited to phosphate esters, phosphazenes, ammonium polyphosphates, melamine phosphates, melamine cyanurates, and metal phosphinates. Examples of phosphazenes include but are not limited to cyclic phosphazene compounds and linear phosphazene compounds. Examples of cyclic phosphazene compounds include but are not limited to hexaphenoxy cyclotriphosphazene. Examples of metal phosphates include but are not limited to the compounds of the following formula (IV):

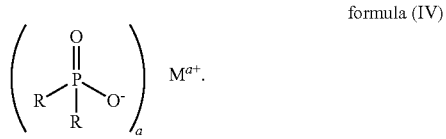

formula (IV)

In formula (IV), each R is independently a $C_1$ to $C_5$ alkyl; $M^{a+}$ is a metal ion selected from the group consisting of $Al^{3+}$, $Zn^{2+}$, $Ca^{2+}$, $Ti^{4+}$, $Mg^{2+}$, $Sr^{2+}$, $Ba^{2+}$, $K^+$, and $Cu^{2+}$; and a is an integer ranging from 1 to 4. Each of the mentioned phosphorus-containing flame retardants can be used either alone or in any combination.

Examples of bromine-containing flame retardants include but are not limited to tetrabromobisphenol A, decabromodiphenyloxide, decabrominated diphenyl ethane, 1,2-bis(tribromophenyl) ethane, brominated epoxy oligomers, octabromotrimethylphenyl indane, bis(2,3-dibromopropyl ether), tris(tribromophenyl) triazine, brominated aliphatic hydrocarbons, and brominated aromatic hydrocarbons. Each of the mentioned bromine-containing flame retardants can be used either alone or in any combination. In the appended examples, decabrominated diphenyl ethane is used as the flame retardant.

In the resin composition of the present invention, based on the total solid content of the resin composition, the content of the flame retardant may range from 0 wt % to 30 wt %, more specifically from 5 wt % to 25 wt %, such as 8 wt %, 10 wt %, 12 wt %, 15 wt %, 18 wt %, 20 wt %, or 23 wt %.

[Filler]

The resin composition may further comprise a filler to improve the mechanical strength, thermal conductivity and dimensional stability of the electronic material prepared therefrom. Suitable filler include but are not limited to fillers selected from the group consisting of silica (including hollow silica), aluminum oxide, magnesium oxide, magnesium hydroxide, calcium carbonate, talc, clays, aluminum nitride, boron nitride, aluminum hydroxide, silicon aluminum carbide, silicon carbide, sodium carbonate, titanium dioxide, zinc oxide, zirconium oxide, quartzes, diamonds, diamond-like carbon, graphites, calcined kaolin, pryan, micas, hydrotalcite, polytetrafluoroethylene (PTFE) powders, glass beads, ceramic whiskers, carbon nanotubes, and nanosized inorganic powders. In the appended examples, silica is used.

In the resin composition of the present invention, based on the total solid content of the resin composition, the content of the filler may range from 0 wt % to 40 wt %, more specifically from 5 wt % to 35 wt %, such as 7 wt %, 8 wt, 10 wt %, 12 wt %, 13 wt %, 15 wt %, 17 wt %, 18 wt %, 20 wt %, 21 wt %, 22 wt %, 23 wt %, 24 wt %, 25 wt %, 26 wt %, 27 wt %, 28 wt %, 29 wt %, 30 wt %, 32 wt %, or 34 wt %.

[Hardening Promoter]

The resin composition of the present invention may further comprise a hardening promoter to promote the curing reaction and to lower the curing reaction temperature of the resin composition. The type of the hardening promoter is not particularly limited as long as it can promote the curing reaction and lower the curing reaction temperature. Suitable hardening promoters include but are not limited to tertiary amines, quaternary ammoniums, imidazoles, and pyridines. Each of the mentioned hardening promoters can either be used alone or in any combination. Examples of tertiary amines include but are not limited to dimethylbenzylamine, 2-(dimethylaminomethyl)phenol, and 2,4,6-tris(dimethylaminomethyl)phenol. Examples of imidazoles include but are not limited to 2-methylimidazole, 2-ethyl-4-methylimidazole, and 2-phenylimidazole. Examples of the pyridines include but are not limited to 2,3-diaminopyridine, 2,5-diaminopyridine, 2,6-diaminopyridine, 4-dimethylaminopyridine, 2-amino-3-methylpyridine, 2-amino-4-methylpyridine, and 2-amino-3-nitropyridine.

In general, based on the total solid content of the resin composition, the content of the hardening promoter may range from 0 wt % to 30 wt %, but the present invention is not limited thereto. Persons having ordinary skill in the art can adjust the amount of the hardening promoter depending on the needs.

1.5. Preparation of Resin Composition

The resin composition of the present invention may be prepared into a varnish for subsequent processing by uniformly mixing the components of the resin composition, including the cross-linking agent (A), the polyphenylene ether resin (B), the catalyst (C) and other optional components, with a stirrer, and dissolving or dispersing the resultant mixture in a solvent. The solvent can be any inert solvent that can dissolve or disperse the components of the resin composition but does not react with the components of the resin composition. For example, solvents that can dissolve or disperse the components of the resin composition include but are not limited to toluene, γ-butyrolactone, methyl ethyl ketone, cyclohexanone, butanone, acetone, xylene, methyl isobutyl ketone, N,N-dimethylformamide (DMF), N,N-dimethylacetamide (DMAc), and N-methylpyrolidone (NMP). Each of the mentioned solvents can be used either alone or in any combination. The content of the solvent in the resin composition is not particularly limited as long as the components of the resin composition can be evenly dissolved or dispersed therein. In the appended examples, toluene is used as the solvent.

2. Prepreg

The present invention also provides a prepreg prepared from the aforementioned resin composition, wherein the prepreg is prepared by impregnating a substrate with the aforementioned resin composition or by coating the aforementioned resin composition onto a substrate and drying the impregnated or coated substrate. For example, the impregnated or coated substrate may be dried at a temperature ranging from 80° C. to 180° C. for 1 to 10 minutes to obtain a semi-cured (B-stage) prepreg. Alternatively, the prepreg may be prepared by using the resin composition to form a film, and then hot-pressing the film with a substrate. The preparing method of a prepreg can be easily accomplished by persons having ordinary skill in the art based on the disclosure of the subject specification and their general knowledge, and it will be illustrated in the appended examples.

Suitable substrates include a glass-fiber reinforcing material, a kraft paper, a short fiber cotton paper, a natural fiber cloth, and an organic fiber cloth. The mentioned substrates can be used in the form of a composite of two or more of them. Examples of the glass-fiber reinforcing material include but are not limited to a glass-fiber cloth, a glass paper, and a glass mat.

In some embodiments of the present invention, a semi-cured prepreg is prepared by using 2116 reinforcing glass-fiber cloth as a reinforcing material (substrate) and heating and drying the reinforcing material at 150° C. for 1 to 5 minutes (B-stage).

3. Laminate

The present invention also provides a laminate prepared from the aforementioned prepreg, which comprises a dielectric layer and a conductive layer covering a surface of the dielectric layer, wherein the dielectric layer is provided by the aforementioned prepreg and the conductive layer may be a metal foil. Examples of the metal foil include but are not limited to a copper foil and an aluminum foil. A copper foil is preferred. When using the prepreg to prepare the laminate, the laminate can be obtained by superimposing a plurality of the abovementioned prepregs, superimposing a metal foil (such as a copper foil) on at least one external surface of the dielectric layer composed of the superimposed prepregs to provide a superimposed object, and then performing a hot-pressing operation onto the superimposed object.

In addition, the aforementioned laminate can form a printed circuit board by further patterning the external conductive layer thereof.

4. Examples 4.1. Testing Method

The present invention is further illustrated by the embodiments hereinafter, wherein the testing instruments and methods are as follows:

[Volatile Component Test]

A prepreg is weighed and then subjected to a heat treatment at 160° C. for 15 minutes. Then, the heated prepreg is weighed again to calculate the weight loss percentage of the prepreg (=[(weight before the heat treatment−weight after the heat treatment)/weight before the heat treatment]× 100%). If the weight loss percentage is lower than 3%, the result of the volatile component test is recorded as "○", meaning that the prepreg passes the volatile component test. If the weight loss percentage is equal to or higher than 3%, the result of the volatile component test is recorded as "x", meaning that the prepreg fails in the volatile component test.

[Dielectric Constant (Dk) and Dissipation Factor (Df) Measurement]

The dielectric constant (Dk) and dissipation factor (Df) of the laminate are measured according to IPC-TM-650 2.5.5.13 under an operating frequency of 10 GHz.

[Glass Transition Temperature (Tg) Test]

A laminate is etched to remove the copper foils on the surfaces of it to obtain a dielectric material. The viscoelasticity of the dielectric material is measured by using a dynamic mechanical analyzer (model: DMA Q800, available from TA Instrument). The conditions for measurement are as follows: the mode is bending mode, the frequency is 10 Hz, the heating rate is 5° C./min, and the measuring temperature ranges from room temperature to 280° C. The Tg is the temperature at which tan δ in the resulting viscoelasticity curve is maximum.

[Pressure Cooker Test (PCT) Thermal Resistance Test]

PCT thermal resistance is also known as moisture absorption thermal resistance, and is tested in accordance with JIS C5012. PCT thermal resistance is used to evaluate the thermal resistance of a solder-floated laminate after laying the laminate at a temperature of 60° C. and a relative humidity of 60% for 120 hours. The solder-floating is performed at a solder bath temperature of 288° C. for 60 seconds. The solder-floated laminate is inspected visually and by an optical microscope (5× or more) to see if there are deficiencies, such as measling or swelling. If no deficiencies such as measling or swelling are found, the result of the PCT thermal resistance test is recorded as "○", meaning that the laminate passes the PCT thermal resistance test. If any deficiencies such as measling or swelling are found, the result of the PCT thermal resistance test is recorded as "x", meaning that the laminate fails in the PCT thermal resistance test.

[Flame Retardance Test]

The flame retardance test is performed according to UL94V (Vertical Burn), wherein a laminate is held vertically and burned by using a Bunsen burner to evaluate its self-extinguishing properties and combustion-supporting properties. The ranking for the flame retardance level is V0>V1>V2.

[Peel Strength Test]

The peel strength of a laminate denotes the bonding strength between its dielectric layer and metal foil which serves as a conductive layer. Herein, the value of peel strength is expressed by the force required for vertically peeling the copper foil (⅛ inch wide) of a laminate from the laminate. The unit of the peel strength is lbf/in.

4.2. List of Raw Materials Used in Examples and Comparative Examples

TABLE 1

List of raw materials

| Model No. of Raw material | Description |
|---|---|
| SA-9000 | A polyphenylene ether resin, whose terminal ends are modified by 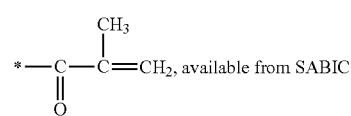, available from SABIC |
| OPE-2St | A polyphenylene ether resin, whose terminal ends are modified by 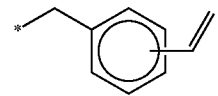, available from MITSUBISHI GAS CHEMICAL |
| Perbutyl P | A catalyst, available from Nippon Oil & Fats (NOF) |
| Ricon 100 | An elastomer, available from CRAY VALLEY |
| Ricon 181 | An elastomer, available from CRAY VALLEY |
| SAYTEX 8010 | A flame retardant, available from ALBERMARLE |
| SC-5500-SVJ | A silica filler, available from ADMATECHS |

4.3. Preparation of Cross-Linking Agent (A)

[Preparation of DAIC-1]

First, 30 g (0.143 mol) of unmodified diallyl isocyanurate was dissolved in 200 ml of DMF to form a solution. Then, 19.8 g (0.143 mol) of potassium carbonate was added into the solution, and the solution was heated by a temperature-controlled oil bath to 50° C. Afterwards, 27.6 g (0.143 mol)

of 1-bromooctane was added over 10 minutes into the solution to obtain a suspension (mixture). The suspension was stirred and heated to 120° C. to react for 4 hours, and the mixture was then cooled to room temperature. After the reaction was determined as complete, the mixture was subjected to filtering using a filter paper and distilled at 85° C. and 100 mTorr to remove DMF. The residue was then re-dissolved in 250 ml of ethyl acetate and then extracted sequentially by 100 ml of water, 100 ml of 5 vol % hydrochloric acid, and 100 ml of saturated sodium chloride solution. The resultant organic solution was dried over magnesium sulfate, filtered using a filter paper, and distilled at 85° C. and 100 mbar to yield 35 g of a colorless oil. The colorless oil was 1,3-diallyl-5-octyl isocyanurate (hereinafter "DAIC-1"). The structure and $^1$H NMR of DAIC-1 are shown below.

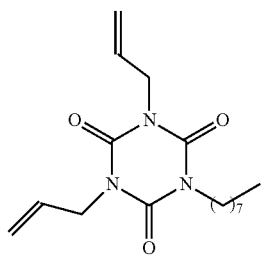

DAIC-1

$^1$H NMR (400 MHz, CDCl$_3$): δ5.84 (m, 2H), 5.14 (m, 4H), 4.35 (d, 2H), 3.74 (t, 2H), 1.54 (t, 2H), 1.26 (m, 10H), 0.86 (t, 3H).

ESI-MS (m/z, MH$^+$): Calculated value: 321.21 Da; Experimental value: 321.63 Da.

[Preparation of DAIC-2]

The preparation procedures of DAIC-1 were repeated to prepare 1,3-diallyl-5-isooctyl isocyanurate (hereinafter "DAIC-2"), except that 1-bromooctane was replaced by 1-bromo-isooctane, wherein the amount of 1-bromo-isooctane was adjusted such that the molar ratio of diallyl isocyanurate:potassium carbonate:hydrocarbyl bromide was 1:1:1. The structure and $^1$H NMR of DAIC-2 are shown below.

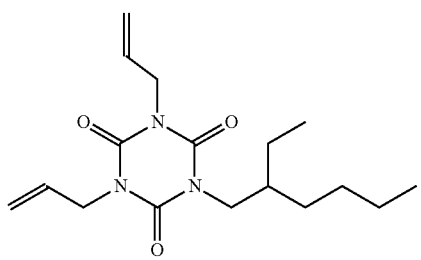

DIAC-2

$^1$H NMR (400 MHz, CDCl$_3$): δ5.83 (m, 2H), 5.17 (m, 4H), 3.85 (d, 4H), 3.24 (m, 1H), 2.99 (m, 1H), 2.10 (m, 1H), 1.29 (m, 8H), 0.96 (t, 6H).

ESI-MS (m/z, MH$^+$): Calculated value: 321.21 Da; Experimental value: 321.54 Da.

[Preparation of DAIC-3]

The preparation procedures of DAIC-1 were repeated to prepare 1,3-diallyl-5-dodecyl isocyanurate (hereinafter "DAIC-3"), except that 1-bromooctane was replaced by 1-bromododecane, wherein the amount of 1-bromododecane was adjusted such that the molar ratio of diallyl isocyanurate:potassium carbonate:hydrocarbyl bromide was 1:1:1. The structure and $^1$H NMR of DAIC-3 are shown below.

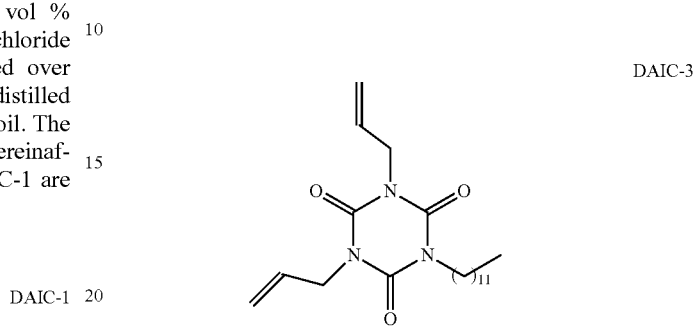

DAIC-3

$^1$H NMR (400 MHz, CDCl$_3$): δ5.89 (m, 2H), 5.28 (m, 4H), 4.50 (d, 2H), 3.89 (t, 2H), 1.65 (t, 2H), 1.27 (m, 18H), 0.90 (t, 3H).

ESI-MS (m/z, MH$^+$): Calculated value: 377.27 Da; Experimental value: 377.13 Da.

[Preparation of DAIC-4]

The preparation procedures of DAIC-1 were repeated to prepare 1,3-diallyl-5-decenyl isocyanurate (hereinafter "DAIC-4"), except that 1-bromooctane was replaced by 10-bromo-1-decene, wherein the amount of 10-bromo-1-decene was adjusted such that the molar ratio of diallyl isocyanurate:potassium carbonate:hydrocarbyl bromide was 1:1:1. The structure and $^1$H NMR of DAIC-4 are shown below.

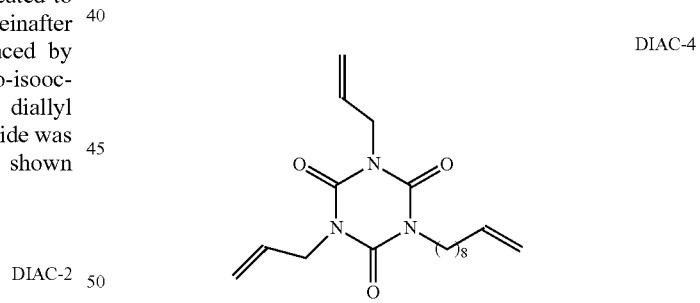

DIAC-4

$^1$H NMR (400 MHz, CDCl$_3$): δ5.78 (m, 3H), 5.21 (m, 4H), 4.85 (m, 2H), 4.43 (d, 4H), 3.80 (t, 2H), 1.96 (m, 2H), 1.54 (m, 2H), 1.24 (m, 10H).

ESI-MS (m/z, MH$^+$): Calculated value: 348.46 Da; Experimental value: 348.13 Da.

4.4. Preparation of Resin Composition

The resin compositions of Examples 1 to 10 and Comparative Examples 1 to 4 were prepared according to the proportions shown in Tables 2-1 to 2-3. Specifically, each of the resin compositions was prepared by mixing the components at room temperature with stirring for 60 minutes, adding toluene (available from FLUKA) as a solvent, and stirring the resultant mixture at room temperature for 60 to 120 minutes to obtain the resin composition.

TABLE 2-1

Composition of the resin compositions of Examples 1 to 5

| | | Example | | | | |
|---|---|---|---|---|---|---|
| Unit: parts by weight | | 1 | 2 | 3 | 4 | 5 |
| Cross-linking agent (A) | DAIC-1 | 30 | | | | 30 |
| | DAIC-2 | | 30 | | | |
| | DAIC-3 | | | 30 | | |
| | DAIC-4 | | | | 30 | |
| Polyphenylene ether resin (B) | SA-9000 | 70 | 70 | 70 | 70 | |
| | OPE-2St | | | | | 70 |
| Catalyst (C) | Perbutyl P | 1 | 1 | 1 | 1 | 1 |
| Flame retardant | SAYTEX 8010 | 20 | 20 | 20 | 20 | 20 |
| Filler | SC-5500-SVJ | 55 | 55 | 55 | 55 | 55 |

TABLE 2-2

Composition of the resin compositions of Examples 6 to 10

| | | Example | | | | |
|---|---|---|---|---|---|---|
| Unit: parts by weight | | 6 | 7 | 8 | 9 | 10 |
| Cross-linking agent (A) | DAIC-1 | 20 | | 25 | 25 | 25 |
| | DAIC-2 | | 55 | | | |
| Polyphenylene ether resin (B) | SA-9000 | 80 | 45 | 60 | 70 | |
| | OPE-2St | | | | | 60 |
| Catalyst (C) | Perbutyl P | 1 | 1 | 1 | 1 | 1 |
| Elastomer | Ricon 100 | | | | 15 | 5 |
| | Ricon 181 | | | | | 10 |
| Flame retardant | SAYTEX 8010 | 20 | 20 | 20 | 20 | 20 |
| Filler | SC-5500-SVJ | 55 | 55 | 55 | 55 | 55 |

TABLE 2-3

Composition of the resin compositions of Comparative Examples 1 to 4

| | | Comparative Example | | | |
|---|---|---|---|---|---|
| Unit: parts by weight | | 1 | 2 | 3 | 4 |
| Cross-linking agent (A) | DAIC-1 | | | 12 | |
| | DAIC-2 | | 50 | | 75 |
| Other component | TAIC | 30 | | | |
| Polyphenylene ether resin (B) | SA-9000 | 70 | | 88 | 25 |
| Catalyst (C) | Perbutyl P | 1 | 1 | 1 | 1 |
| Elastomer | Ricon 100 | | 50 | | |
| Flame retardant | SAYTEX 8010 | 20 | 20 | 20 | 20 |
| Filler | SC-5500-SVJ | 55 | 55 | 55 | 55 |

4.5. Preparation and Property Measurements of Laminates

Prepregs and laminates were prepared respectively by using the resin compositions of Examples 1 to 10 and Comparative Examples 1 to 4. First, glass fiber cloths (Model No.: 2116; thickness: 0.094 mm) were immersed in the resin compositions of Examples 1 to 10 and Comparative Examples 1 to 4 respectively through roll coaters, and the thicknesses of the glass fiber cloths were controlled to a proper extent. The immersed glass fiber cloths were then placed in an oven and heated and dried at 150° C. for 3 minutes to produce prepregs in a semi-cured state (B-stage). Afterwards, two sheets of copper foils (each 0.5 oz.) were respectively superimposed on both of the two external surfaces of the prepregs, and then the prepared objects were placed in a hot press machine to be cured through a high temperature hot-pressing. The hot-pressing conditions were as follows: heating to 200° C. to 220° C. at a heating rate of 3.0° C./min, and hot-pressing at 200° C. to 220° C. for 180 minutes under a full pressure of 15 kg/cm² (the initial pressure was 8 kg/cm²).

The properties of the prepregs and laminates of Examples 1 to 10 and Comparative Examples 1 to 4, including volatile component, Dk, Df, Tg, peel strength, flame retardance, and PCT thermal resistance, were evaluated according to the aforementioned testing methods, and the results are listed in Tables 3-1 to 3-3.

TABLE 3-1

Properties of prepregs and laminates of Examples 1 to 5

| | | Example | | | | |
|---|---|---|---|---|---|---|
| | Unit | 1 | 2 | 3 | 4 | 5 |
| Tg | °C. | 206 | 208 | 203 | 209 | 208 |
| Peel strength | lbf/in | 3.4 | 3.3 | 3.2 | 3.5 | 3.5 |
| Volatile component | | ◯ | ◯ | ◯ | ◯ | ◯ |
| Dk @ 10 GHz | | 3.9 | 3.9 | 3.8 | 3.9 | 3.9 |
| Df @ 10 GHz | | $4.9 \times 10^{-3}$ | $4.8 \times 10^{-3}$ | $4.6 \times 10^{-3}$ | $5.0 \times 10^{-3}$ | $5.0 \times 10^{-3}$ |
| PCT thermal resistance | | ◯ | ◯ | ◯ | ◯ | ◯ |
| Flame retardance | | V-0 | V-0 | V-0 | V-0 | V-0 |

TABLE 3-2

Properties of prepregs and laminates of Examples 6 to 10

| | | Example | | | | |
|---|---|---|---|---|---|---|
| | Unit | 6 | 7 | 8 | 9 | 10 |
| Tg | °C. | 214 | 200 | 215 | 210 | 213 |
| Peel strength | lbf/in | 3.2 | 3.1 | 4.3 | 4.0 | 3.9 |
| Volatile component | | ◯ | ◯ | ◯ | ◯ | ◯ |
| Dk @ 10 GHz | | 3.8 | 3.9 | 3.8 | 3.9 | 3.8 |
| Df @ 10 GHz | | $4.6 \times 10^{-3}$ | $5.6 \times 10^{-3}$ | $3.9 \times 10^{-3}$ | $4.7 \times 10^{-3}$ | $4.2 \times 10^{-3}$ |
| PCT thermal resistance | | ◯ | ◯ | ◯ | ◯ | ◯ |
| Flame retardance | | V-0 | V-0 | V-0 | V-0 | V-0 |

TABLE 3-3

Properties of prepregs and laminates of Comparative Examples 1 to 4

| | | Comparative Example | | | |
|---|---|---|---|---|---|
| | Unit | 1 | 2 | 3 | 4 |
| Tg | °C. | 215 | Not applicable | 218 | 185 |
| Peel strength | lbf/in | 3.0 | 2.5 | 2.4 | 2.7 |
| Volatile component | | ✕ | ◯ | ◯ | ◯ |
| Dk @ 10 GHz | | 3.9 | 3.8 | 3.9 | 4.0 |
| Df @ 10 GHz | | $5.9 \times 10^{-3}$ | $4.0 \times 10^{-3}$ | $4.5 \times 10^{-3}$ | $6.2 \times 10^{-3}$ |
| PCT thermal resistance | | ◯ | ✕ | ◯ | ✕ |
| Flame retardance | | V-0 | V-0 | V-0 | V-0 |

As shown in Tables 3-1 and 3-2, each of the electronic materials prepared from the resin composition of the present invention exhibits satisfactory physicochemical properties and dielectric properties (e.g., Dk, Df, Tg, PCT thermal resistance, etc.), and has outstanding peel strength (3.1 lbf/in or more). In addition, the prepreg prepared by using the resin composition of the present invention can pass the volatile component test, thereby reducing difficulties during processing. Specifically, Examples 1 to 7 show that when the cross-linking agent (A) has the structure of formula (I) and the weight ratio of the polyphenylene ether resin (B) to the cross-linking agent (A) is within the designated range, the resultant electronic materials can be provided with satisfactory physicochemical properties and dielectric properties, especially outstanding peel strength. Examples 8 to 10 also show that, when the resin composition further comprises an elastomer, the peel strength of the resultant electronic materials can be further improved.

By contrast, as shown in Table 3-3, the electronic materials prepared by using resin compositions other than the resin composition of the present invention cannot provide the inventive efficacy of the present invention. They do not have entirely satisfactory physicochemical properties and dielectric properties, and they also do not have outstanding peel strength. Specifically, Comparative Example 1 shows that the prepreg prepared by using a TAIC-containing resin composition cannot pass the volatile component test. Comparative Example 2 shows that when the resin composition does not comprise polyphenylene ether resin and the cross-linking agent (A) with a specific structure of formula (I) simultaneously, the resultant electronic material cannot have good thermal resistance and peel strength. Comparative Examples 3 and 4 show that when the weight ratio of the polyphenylene ether resin (B) to the cross-linking agent (A) is outside the designated range (e.g., higher than 5 or lower than 0.5), the resultant electronic materials cannot have good thermal resistance and peel strength simultaneously.

The above examples are used to illustrate the principle and efficacy of the present invention and show the inventive features thereof, but are not used to limit the scope of the present invention. People skilled in this field may proceed with a variety of modifications and replacements based on the disclosures and suggestions of the invention as described without departing from the principle and spirit thereof. Therefore, the scope of protection of the present invention is that as defined in the claims as appended.

What is claimed is:
1. A resin composition, which comprises:
(A) a cross-linking agent of the following formula (I):

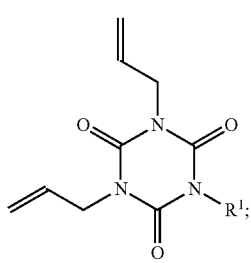

formula (I)

(B) a polyphenylene ether resin, wherein the terminal ends of the polyphenylene ether resin are independently modified by a substituent with a carbon-carbon double bond; and
(C) a catalyst,
wherein,
in formula (I), $R^1$ is a $C_6$ to $C_{16}$ alkenyl; and
the weight ratio of the polyphenylene ether resin (B) to the cross-linking agent (A) ranges from 0.5 to 5.
2. The resin composition of claim 1, wherein $R^1$ in formula (I) is a $C_8$ to $C_{14}$ alkenyl.
3. The resin composition of claim 1, wherein the cross-linking agent (A) is,

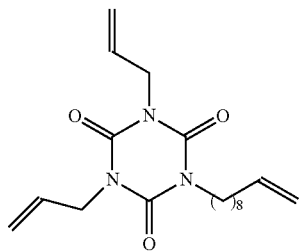

4. The resin composition of claim 1, wherein the substituent with a carbon-carbon double bond is represented by the following formula (III):

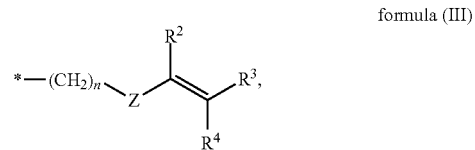

formula (III)

in formula (III),
$R^2$, $R^3$ and $R^4$ are independently H or a substituted or unsubstituted $C_1$ to $C_6$ alkyl;
Z is

or an arylene;
n is an integer ranging from 0 to 10; and
* denotes the bonding site to the terminal end of the polyphenylene ether resin.
5. The resin composition of claim 4, wherein the substituent with a carbon-carbon double bond is

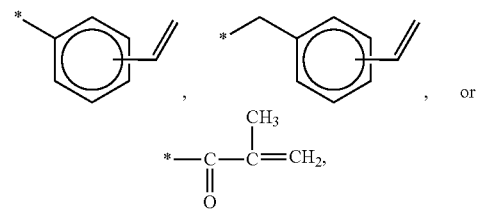

wherein * denotes the bonding site to the terminal end of the polyphenylene ether resin.
6. The resin composition of claim 1, wherein the catalyst (C) is an organic peroxide.
7. The resin composition of claim 6, wherein the organic peroxide is selected from the group consisting of dicumyl peroxide, tert-butyl peroxybenzoate, di-tert-amyl peroxide (DTAP), isopropylcumyl-tert-butyl peroxide, tert-butylcumylperoxide, di(isopropylcumyl) peroxide, di-tert-butyl peroxide, α,α'-bis(tert-butylperoxy)diisopropyl benzene, benzoyl peroxide (BPO), 1,1-bis(tert-butylperoxy)-3,3,5-trimethylcyclohexane, butyl 4,4-di(tert-butylperoxy) valerate, 2,5-dimethyl-2,5-di(tert-butylperoxy) hexane, 2,5-dimethyl-2,5-di(tert-butylperoxy)-3-hexyne, and combinations thereof.

8. The resin composition of claim 1, wherein the weight ratio of the polyphenylene ether resin (B) to the crosslinking agent (A) ranges from 0.8 to 4.

9. The resin composition of claim 1, further comprising one or more additives selected from the group consisting of an elastomer, a flame retardant, a filler, a hardening promoter, a dispersing agent, a toughener, a viscosity modifier, a thixotropic agent, a defoaming agent, a leveling agent, a surface treating agent, a stabilizer, and an antioxidant.

10. The resin composition of claim 9, wherein the elastomer is selected from the group consisting of polybutadiene, polyisoprene, a styryl-containing polymer, and combinations thereof.

11. The resin composition of claim 10, wherein the elastomer is a butadiene-styrene copolymer or an isoprene-styrene copolymer.

12. The resin composition of claim 9, wherein the flame retardant is a phosphorus-containing flame retardant, a bromine-containing flame retardant, or a combination thereof.

13. The resin composition of claim 9, wherein the filler is selected from the group consisting of silica, aluminum oxide, magnesium oxide, magnesium hydroxide, calcium carbonate, talc, clays, aluminum nitride, boron nitride, aluminum hydroxide, silicon aluminum carbide, silicon carbide, sodium carbonate, titanium dioxide, zinc oxide, zirconium oxide, quartzes, diamonds, diamond-like carbon, graphites, calcined kaolin, pryan, micas, hydrotalcite, polytetrafluoroethylene (PTFE) powders, glass beads, ceramic whiskers, carbon nanotubes, nanosized inorganic powders, and combinations thereof.

14. A prepreg, which is prepared by impregnating a substrate with the resin composition of claim 1 or by coating the resin composition of claim 1 onto a substrate and drying the impregnated or coated substrate.

15. The prepreg of claim 14, wherein the substrate is selected from the group consisting of a glass fiber cloth, a kraft paper, a short fiber cotton paper, a natural fiber cloth, an organic fiber cloth, and a composite of two or more of the foregoing.

16. A laminate, which comprises a dielectric layer and a conductive layer covering the surface of the dielectric layer, wherein the dielectric layer is provided by the prepreg of claim 15.

17. The laminate of claim 16, wherein the conductive layer is a copper foil.

18. A laminate, which comprises a dielectric layer and a conductive layer covering the surface of the dielectric layer, wherein the dielectric layer is provided by the prepreg of claim 14.

19. The laminate of claim 18, wherein the conductive layer is a copper foil.

* * * * *